United States Patent [19]
Milla et al.

[11] Patent Number: 6,057,175
[45] Date of Patent: May 2, 2000

[54] METHOD OF MAKING ENCAPSULATED PACKAGE

[75] Inventors: Juan G. Milla, Mesa; Mark R. Boone, Gilbert, both of Ariz.

[73] Assignee: Medtronic, Inc., Minneapolis, Minn.

[21] Appl. No.: 09/285,365

[22] Filed: Apr. 2, 1999

Related U.S. Application Data

[62] Division of application No. 08/984,721, Dec. 4, 1997.

[51] Int. Cl.$^7$ ................................................. H01L 21/44
[52] U.S. Cl. ........................... 438/113; 438/126; 438/127
[58] Field of Search .................................... 438/113, 126, 438/127, 458, 460

[56] References Cited

U.S. PATENT DOCUMENTS

| | | | |
|---|---|---|---|
| 3,987,012 | 10/1976 | Statton | 528/75 |
| 4,681,656 | 7/1987 | Byrum | 156/645 |
| 4,739,448 | 4/1988 | Rowe et al. | 361/386 |
| 5,061,657 | 10/1991 | Queen et al. | 438/126 |
| 5,171,769 | 12/1992 | Bull et al. | 528/107 |
| 5,285,352 | 2/1994 | Pastore et al. . | |
| 5,490,324 | 2/1996 | Newman | 438/126 |
| 5,528,135 | 6/1996 | Kawamura et al. | 324/158.1 |
| 5,654,243 | 8/1997 | Yoneda et al. | 438/126 |
| 5,729,437 | 3/1998 | Hashimoto | 438/126 |
| 5,756,380 | 5/1998 | Berg et al. | 528/126 |
| 5,763,911 | 6/1998 | Matthew et al. | 257/301 |
| 5,776,798 | 7/1998 | Quan et al. | 438/460 |
| 5,834,835 | 11/1998 | Maekawa | 257/680 |

OTHER PUBLICATIONS

Byrum, J.E. et al., "Manufacturing Low Cost Chip Carriers", pp. 309–314.

"Chipcon(TM) '97", *CHIPCON '97 Papers*, pp. 1–2 (1997).

"Kyocera: Chip Scale Packaging (CSP)", obtained from the internet at http://www.kyocera.com/kai/csp/html, pp. 1 (1997).

"Kyocera: Thin Film", obtained from the internet at http://www.kyocera.com/kai/thinfilm.html, pp. 1–2 (1997).

Lanzone, R., "Ceramic CSP: A Low Cost, Adaptive Interconnect, High Density Technolgy", brochure from CHIPCON™ '97, Semiconductor Technology Center, Inc., pp. 18–25, 31 (1997).

Levine, B., "Chip–Scale Packaging Blooms", *Electronic News*, pp. 1–4 (1996). [obtained from http://www.sumnet.com/enews/front/0916f3.html].

Lomerson, R.B., "High Technology Microcircuit Packaging: Part II", *General Dynamics Corporation: Integrated Circuits Laboratory*, pp. 218–228 (1984).

"Micro Substrates Corporation", obtained from the internet at http://www.cci–msc.com/msc/vpcsp.htm, pp. 1–4 (1997).

"SAMSUNG SRAM: SAMSUNG CSP (Chip Scale Package)", obtained from http://www.sec.samsung.com/Products/sram/csp.html pp. 1–7 (1997).

Solberg, V., "Standards and Applications for Chip Scale Packaging", *Standards and Applications for Chip Scale Packaging* pp. 1–12(1997). [obtained from http://www.t-essera.com/reference/techpapers/–SACSP.HTM].

*Primary Examiner*—Kevin M. Picardat
*Attorney, Agent, or Firm*—Thomas F. Woods; Girma Wolde-Michael; Harold R. Patton

[57] ABSTRACT

An encapsulated package includes a substrate having one or more conductive vias defined therethrough from a first side of the substrate to a second side of the substrate. Conductive bond pads are formed on the first side of the substrate in electrical contact with the one or more conductive vias and conductive package connection pads are formed on the second side of the substrate in electrical contact with the one or more conductive vias. A high voltage component is electrically connected to the conductive bond pads and an encapsulating material is formed over the first side of the substrate including the high voltage component and the conductive bond pads. The encapsulating material has a dielectric strength sufficient for use to block high voltages used in operation of the high voltage components. Further, a method of production allows for mass production of such encapsulated packages.

15 Claims, 11 Drawing Sheets

METHOD OF MAKING ENCAPSULATED PACKAGE

This application is a divisional application of U.S. patent Appln. Ser. No. 08/984,721 filed Dec. 4, 1997 entitled "Encapsulated Package and Method for Making Same" to Milla et al.

FIELD OF THE INVENTION

The present invention relates to component packaging. More particularly, the present invention relates to chip scale packaging for components, e.g., high voltage components such as for use in implantable medical devices.

BACKGROUND OF THE INVENTION

The development and manufacturing of electronic products is continually being challenged by a growing market demand for smaller, more efficient, and a higher performance product. The current trend toward miniaturization is driven to a large extent by portable electronic product applications. However, other product categories are under pressure to reduce size as well, such as in the medical device industry where reliability also must be assured. There are numerous packaging techniques that have been used in the past. For example, some of such techniques include dual in-line packaging (DIP), leadless chip carrier processing, leaded molded plastic packaging, surface mount processing, etc.

In addition, more recently, chip scale packaging (CSP) has been introduced. Generally, CSP includes the packaging of integrated circuits in packages which are slightly larger than the integrated circuits being packaged. Ceramic chip scale packaging (CCSP) includes the use of ceramic substrates in such chip scale packaging of die.

Such conventionally available packaging processes are generally inadequate for packaging many devices, e.g., such currently available packages do not provide adequate characteristics or functionality when used to package high voltage dies. For example, many of the packages conventionally available, such as DIP packages, do not provide surface mount capabilities and are in general much larger than the die being packaged.

High voltage dies have been traditionally packaged in leadless chip carriers and large leaded molded plastic packages (e.g., TO220, SOT23, etc.). Although other packaging options are available (e.g., micro surface mount technology), such packaging options require additional wafer level processing to implement, such as metal passivation and deposition steps, plasma etch steps, etc. Further, many of such packaging options will not work with a high voltage die because in many circumstances, back side or bottom surface contact for such a die (e.g., a field effect transistor die) is not available, the deposited metal is generally too thin too handle current requirements of such high voltage components, such packages cannot withstand the voltage stress levels presented, etc.

Table 1 below lists U.S. Patents that describe a couple of packaging options:

TABLE 1

| U.S. Pat. No. | Inventor(s) | Issue Date |
| --- | --- | --- |
| 4,681,656 | Byrum | 21 July 1987 |
| 5,528,135 | Kawamura et al. | 18 June 1996 |

All patents listed in Table 1, and elsewhere herein, are hereby incorporated by reference in their respective entirety. As those of ordinary skill in the art will appreciate readily upon reading the Summary of the Invention, Detailed Description of the Embodiments, and claims set forth below, many of the devices and methods disclosed in the patents of Table 1 may be modified advantageously by using the teachings of the present invention.

SUMMARY OF THE INVENTION

The present invention has certain objects. That is, various embodiments of the present invention provide solutions to one or more problems existing in the prior art with respect to the packaging of high voltage components including high voltage die and high voltage surface mount components. One such problem is obtaining a desired reliability level for such a package, particularly a package used in implantable medical devices. Further, with regard to the packaging of such high voltage components, the ability to obtain a package that has a low package to component size ratio is problematic. Likewise, the lack of a small (CSP) package having sufficient dielectric strength to provide adequate breakdown protection for high voltage components is also apparent. Yet further, processing methods for packaging high voltage components efficiently while providing the necessary required characteristics for high voltage component packages are also lacking. Conventional processing and packaging techniques have not provided such efficient manufacturing capability for high voltage components.

Various embodiments of the present invention have the object of solving at least one of the foregoing problems. For example, to provide an encapsulated package having a package to component size ratio falling in the range of about 1.2 to about 3.0, e.g., chip scale packaging, a substrate layer having one or more conductive vias defined therethrough is used. The vias extend from a first side of the substrate to a second side of the substrate where package connection pads are provided for mounting the resulting package to a printed circuit board or the like such as by surface mounting processes, e.g., solder paste and reflow. The vias electrically connect a high voltage component mounted on the first side of the substrate to the package connection pads. The high voltage components are connected to the vias at the first side of the substrate, for example, using die bonding or wire bonding techniques. An encapsulating material encapsulates the elements on the first side of the substrate, e.g., the bond pads, wires used for wire bonding, the component, etc.

In addition, to prevent breakdown problems, an encapsulating material having a dielectric strength greater than 100 volts per mil may be used. For high voltage components operable at voltages greater than about 100 volts, encapsulating material having a dielectric strength greater than 400 volts per mil may be used.

In another embodiment of the invention, a plurality of packages are formed by attaching high voltage components in an array of substrate device formation regions of a substrate in a manner such as described above. Thereafter, encapsulating material is formed over the entire structure, and the encapsulated array of substrate device formation regions are singulated to form a plurality of packages. In such a manner, efficient packaging of multiple high voltage components can be achieved.

DETAILED DESCRIPTION OF THE EMBODIMENTS

Figure 1:
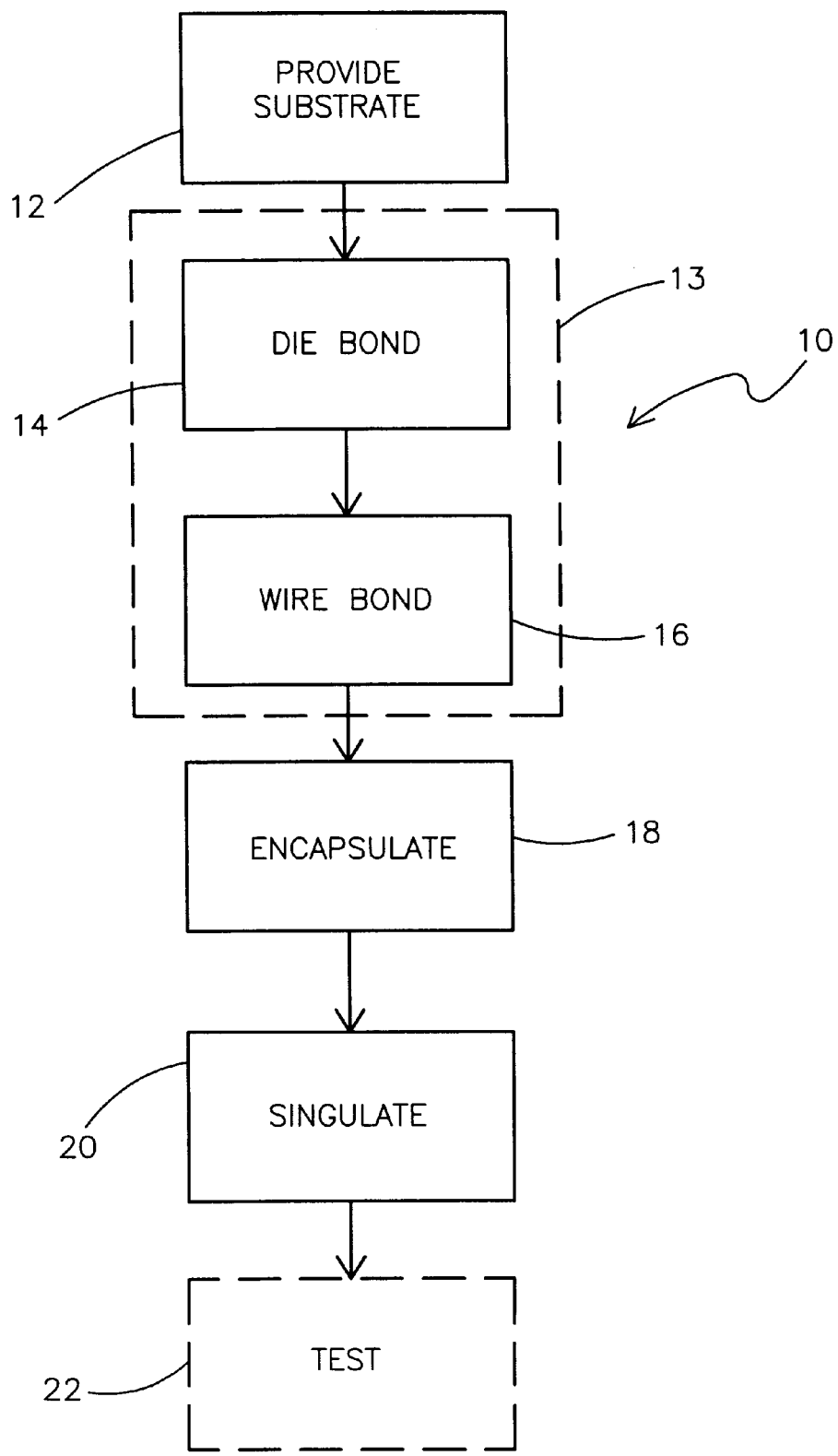
FIG. 1 is a flow diagram of a chip scale packaging method for high voltage components in accordance with the present invention.

Throughout the several figures in this description, like reference numerals designate like elements. FIG. 1 shows an illustrative block diagram of a chip scale package method 10 according to the present invention. The packaging method 10 is particularly beneficial in packaging high voltage discrete die and other high voltage components with low pin counts into a chip scale surface-mountable package. However, one skilled in the art will recognize that other die and components may be packaged in like manners. The packaging of high voltage components in accordance with the method 10 of FIG. 1 provides a packaged device (e.g., encapsulated package 30 of FIG. 2) for use in a variety of applications.

As used herein, a high voltage component refers to an electronic component or device that is operable with a potential greater than about 50 volts across any two electrical terminals or contacts of the component. Such high voltage components may further be operable at DC voltages greater than about 100 volts, and even further may be operable at DC voltages greater than about 300 volts, 500 volts, 1000 volts and even greater.

Such high voltage components include, but clearly are not limited to, high voltage die and high voltage surface mount components. Such components have two or more electrical contact regions associated therewith. Such contact regions, e.g., active contact regions of die, surface mount pads of surface mount components, or die etc., may be located at any position on the high voltage component, e.g., back side, front side, edge, etc.

High voltage die refers generally to solid state switching device, capacitors, resistors, rectifiers, or any other solid state electronic device formed using semiconductor processing techniques. For example, such high voltage die may include devices such as field effect transistors (FETs), metal oxide semiconductor FETs (MOSFETs), insulated gate FETs (IGFETs), thyristors, bipolar transistors, diodes, MOS-controlled thyristors, resistors, etc. Further characteristics of a high voltage die may include the ability to switch or conduct large currents, vertical current flow from the bottom or backside of the die to the top surface or front side of the die, and/or active pads or contacts on both the top and bottom surfaces of the die.

Figure 15:
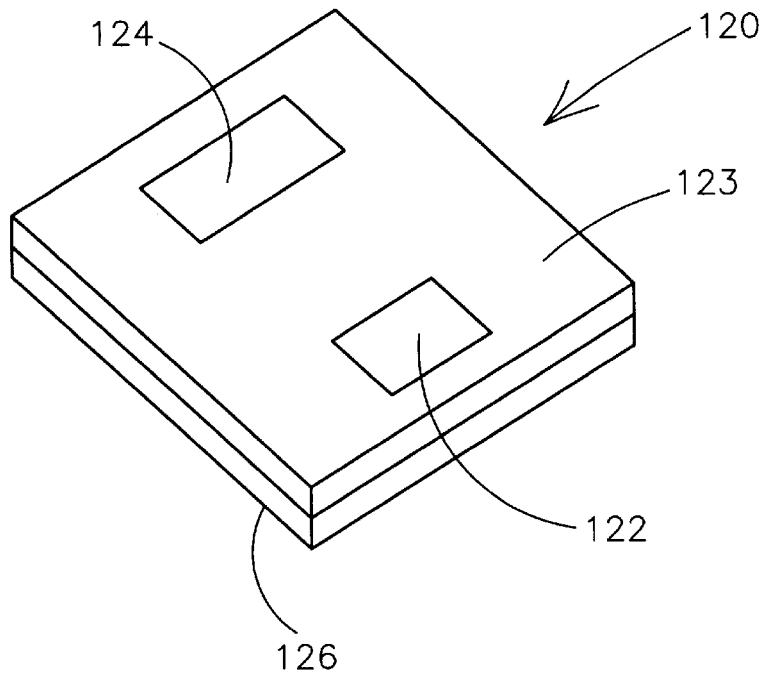
FIG. 15 is one illustrative embodiment of a high voltage die to be packaged in accordance with the present invention.

FIG. 15 shows an illustrative FET die 120 which can be packaged according to the present invention. The FET die 120 includes electrically connectable contact regions on both the back side and front side of the die. The FET die 120 includes connectable contact regions 122, 124 connected to an active portion of the die (e.g., gate, source, or drain) on the front side 123 of the die 120 and a connectable back side 126 which is electrically connected to another active portion (e.g., gate, source, drain) of the die 120.

High voltage surface mount components are generally high voltage devices packaged using surface mount packaging techniques which are operable at the voltages set forth above. For example, such high voltage surface mount components include, but are clearly not limited to, chip components such as chip capacitors and chip resistors, thermistors, inductors, zener diode surge suppressers, chip capacitor and chip resistor arrays, etc.

Figure 16:
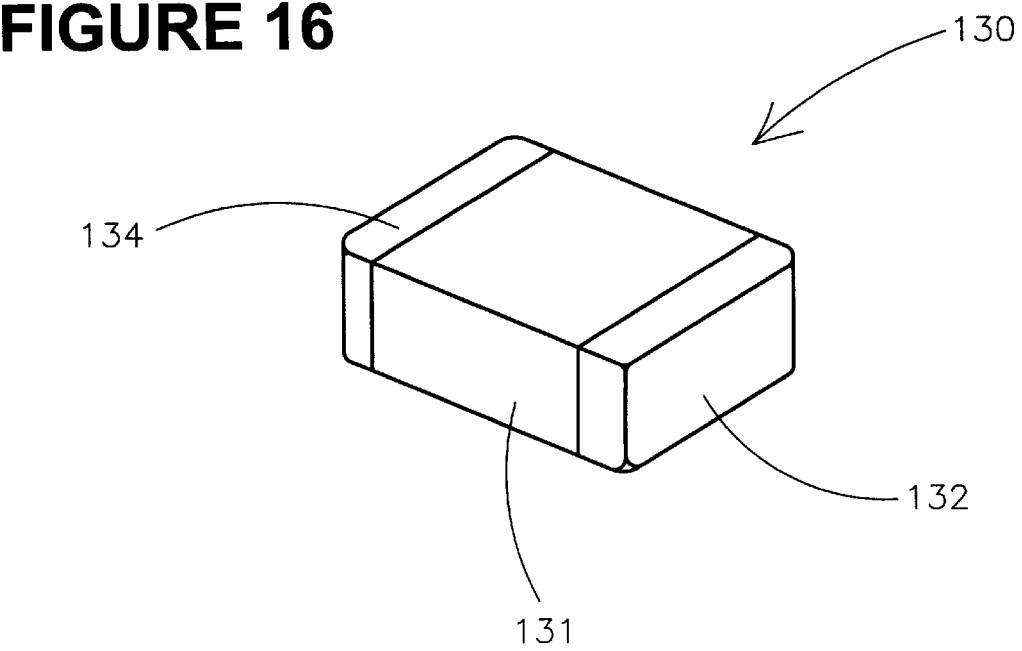
FIG. 16 is one illustrative embodiment of a high voltage surface mount component to be packaged in accordance with the present invention.

FIG. 16 shows an illustrative high voltage surface mount component 130 (a capacitor) that can be repackaged according to the present invention. The surface mount component 130 includes a ceramic body portion 131 having contact regions 132, 134 at opposing ends thereof.

Although the present invention is particularly beneficial for use in packaging discrete high voltage die as defined above, the present invention also has particular advantages in the repackaging of high voltage surface mount components. For example, such repackaging takes advantage of the high voltage breakdown strength of the encapsulanting material used according to the present invention so to provide suppression of surface arcing. In the case of repackaging high voltage surface mount components, such surface mount components would typically be electrically connected to the substrate by processes such as soldering and reflow techniques, as opposed to wire and die bonding. Such solder and reflow techniques are conventionally used for mounting surface mount components to a printed circuit board.

Figure 14:
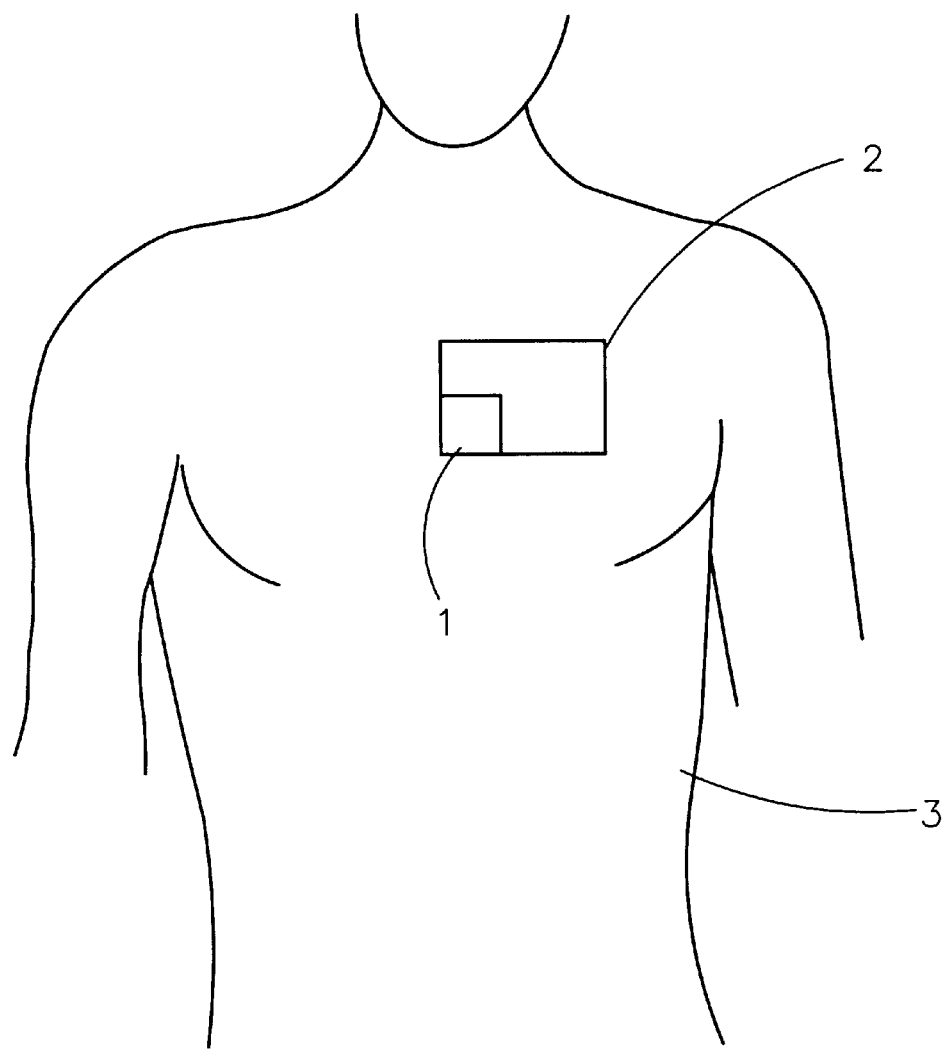
FIG. 14 is a general diagram showing a body having an implantable medical device including an encapsulated package incorporated therein as processed in accordance with the present invention.

The present invention provides encapsulated packages which are particularly beneficial for use in implantable medical devices 2 as shown in FIG. 14. FIG. 14 generally shows an implantable medical device 2 powered by an electrochemical cell 1, or battery. The implantable medical device 2 includes a component packaged according to the present invention and may be any medical device implanted in a human body 3. For example, such medical devices may include heart pacemakers, tachyarrhythmia devices such as defibrillators, any implantable pulse generator devices, drug delivery devices, neurostimulators, etc. In accordance with the following description, it will be evident that the present invention is applicable for use in any implantable medical device. High voltage components, e.g. high voltage diodes packaged by the method as shown in FIG. 1 may be particularly advantageous for use as low-power or pulsed applications, e.g., high voltage blocking and low duty cycle switching applications.

The chip scale packaging method 10, as shown in FIG. 1, includes providing a substrate 12. At least one high voltage component is then electrically connected to bond pads on the substrate (block 13). For example, the high voltage component may be electrically connected by die bonding (block 14), and/or wire bonding (block 16) of contact regions of the component to the bond pads on the substrate. The structure formed using the previous steps is then encapsulated (block 18). Thereafter, if more than one package is being formed, the various encapsulated packages are singulated (block 20). Once the component is packaged, the packaged component can be optionally burned-in and tested without damage to the component (block 22), and further may be reworked at the board level. The burn-in and test flexibility allows implementation of high level known-good die processes. If components are packaged using the packaging method 10, an entire hybrid circuit can be built with surface mount components making all the components of the hybrid circuit reworkable.

The substrate provided (block 12) may be any organic or inorganic substrate having conductive vias defined therethrough. For example, the substrate may be a ceramic substrate (e.g., single layer ceramic substrate, multilayer ceramic substrate, ceramic substrate with vias completely filled with conductive material, etc.) or any printed wiring board (PWB) (e.g., a laminate structure, a single layer organic material, a PWB with plated through hole vias, etc.)

Figure 4:
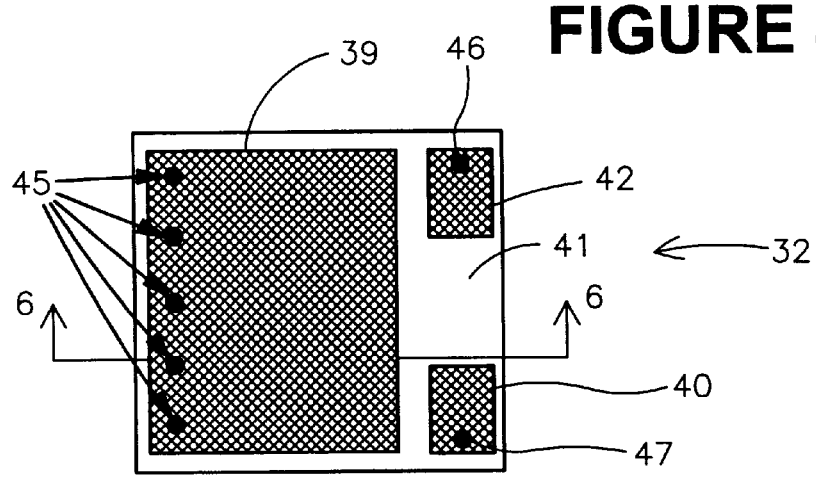
FIG. 4 is a top view of one illustrative embodiment of a ceramic substrate used in the method of FIG. 1.
Figure 5:
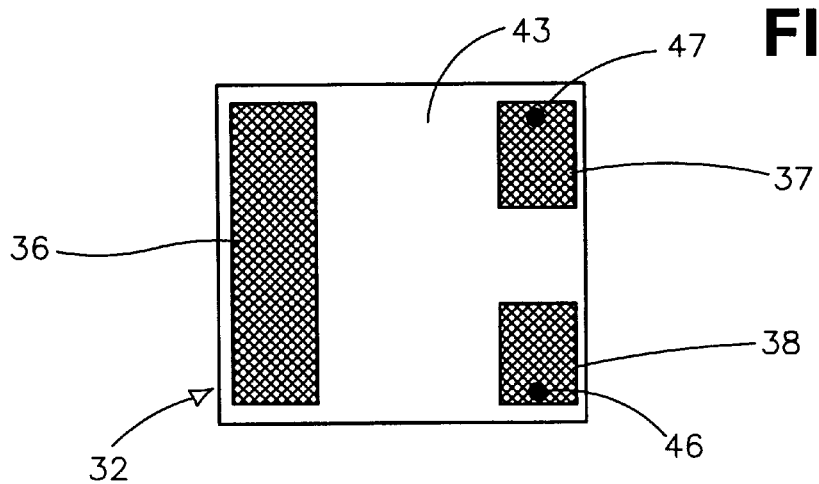
FIG. 5 is a bottom view of the ceramic substrate of FIG. 4.
Figure 6:
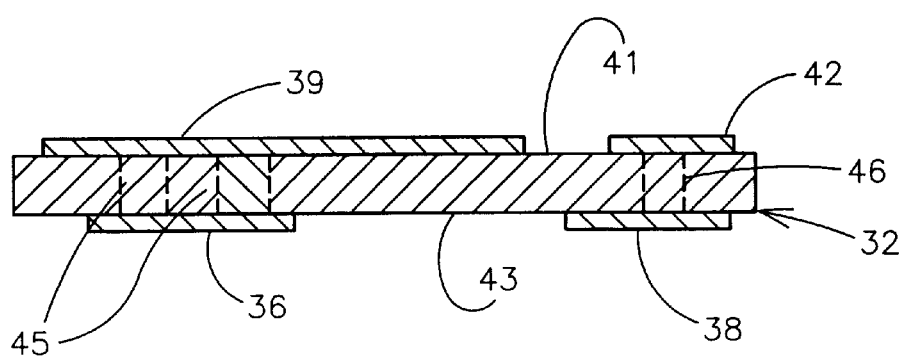
FIG. 6 is a cross-section view taken at line 6—6 of the ceramic substrate of FIG. 4.

FIGS. 4–6 illustrate one embodiment of a ceramic substrate 32 provided according to the present invention. The ceramic substrate 32 is a single layer ceramic substrate provided with a via pattern drilled therein. The illustrative ceramic substrate 32, shown in FIG. 4, includes vias 45, via 46, and via 47. The thickness of the single layer ceramic layer substrate 32 will vary. Preferably, the thickness of the substrate is about 0.020 inches (0.51 millimeters) +/−20 percent. The via hole diameters vary depending on the current carrying capability required by the high voltage die 56 (shown in FIG. 8) mounted thereon. For example, the via hole diameters may be about 0.010 inches (0.254 millimeters) +/−20 percent.

As will be described further below with reference to FIGS. 11–13, the ceramic substrate 32 shown in FIGS. 4–6 may be one of an array of ceramic substrate device formation regions. With use of such an array, mass production of encapsulated packages is allowed.

Using thick film processing, the vias 45–47 are entirely filled with conductive paste to serve as the interconnect between a first side 41 (top side) and a second side 43 (bottom side) of ceramic substrate 32. The conductive paste is preferably a gold paste but may also be or include other electrical interconnect materials or any other suitable conductive paste, such as platinum, palladium, silver, or any combination thereof. The vias 45–47 are completely filled to prohibit encapsulant from advancing into such vias during later processing.

With the vias 45–47 filled with conductive paste, various conductive pads are then printed on the first side 41 and second side 43 of the ceramic substrate 32. As shown in FIG. 4, a die bond pad 39 is printed on first side 41 of ceramic substrate 32. Further, wire bond pads 42, 40 are formed in electrical contact with vias 46, 47 on first side 41 of ceramic substrate 32. The die bond pad 39 and wire bond pads 42, 40 may be screen printed on the first side 41 of the ceramic substrate 32 or provided thereon by any other contact pad formation process. Preferably, the material forming such bond pads is gold, but the material may be or include any other electrical interconnect materials such as platinum, palladium, silver, or any combination thereof.

Solderable package connection pads 36–38 are printed on the second side 43 of the ceramic substrate 32. As shown in FIG. 5, solderable package connection pads 36–38 are formed on the second side 43 of ceramic substrate 32 over and in electrical contact with vias 45–47. Package connection pad 36 is printed in electrical contact with vias 45 which extend to die bond pad 39 and solderable package connection pads 38, 37 are formed in electrical contact with vias 46, 47 which extend to wire bond pads 42, 40, respectively. The solderable connection pads 36–38 are also preferably screen printed on the second side 43 of ceramic substrate 32 and are preferably formed of gold but may also be or include other electrical interconnect materials such as platinum, palladium, silver, or any combination thereof. Any materials that can withstand soldering processes are suitable. The package connection pads 36–38 are similar to pads described in the literature as land grid array pads (LGA) and are designed to be solderable directly to a board using a solder paste. In other words, no solder bumping is required. It should be readily apparent that various other types of solderable package connection pads, such as those requiring solder bumping, may be used for providing an electrical connection of the encapsulated package (FIG. 2) to a printed circuit board.

FIG. 6 shows a cross-section view taken at line 6—6 of FIG. 4. FIG. 6 illustrates the connection of the die bond pad 39 to the solderable package connection pad 36 by vias 45. Further, connection of wire bond pad 42 to solderable package connection pad 38 by via 46 is also shown.

Figure 7:
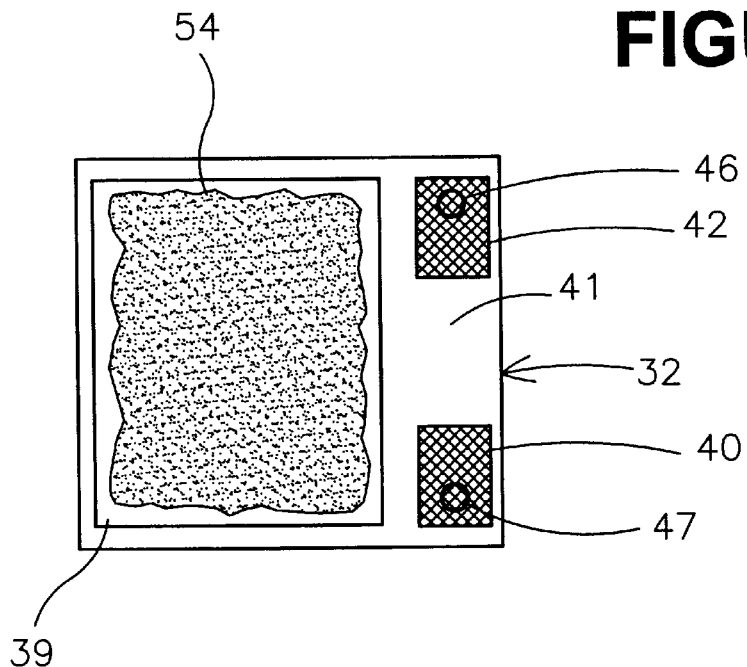
FIG. 7 is a top view of the ceramic substrate of FIG. 4 having a conductive material provided thereon.
Figure 8:
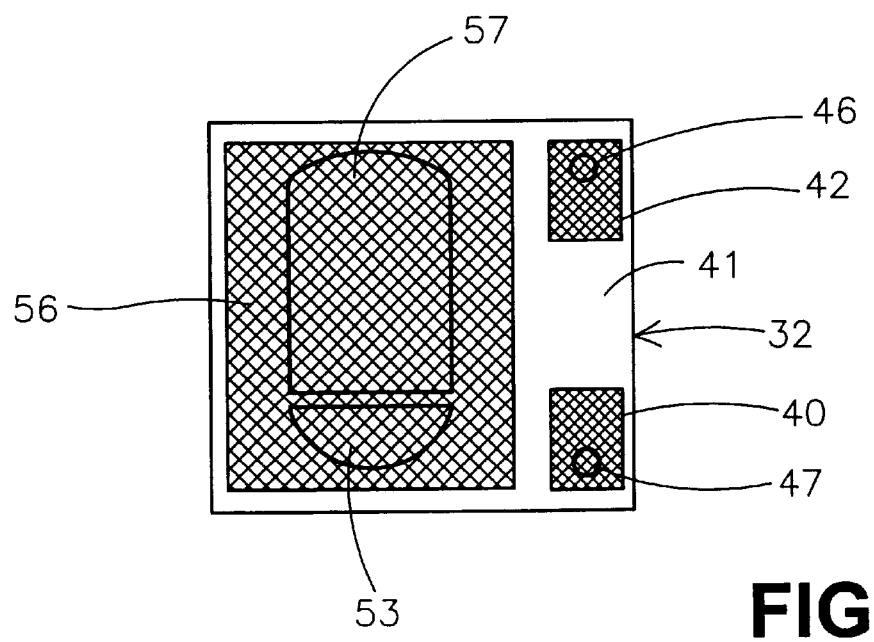
FIG. 8 is a top view of the structure shown in FIG. 7 further including a die positioned on the conductive material for die bonding thereof.
Figure 9:
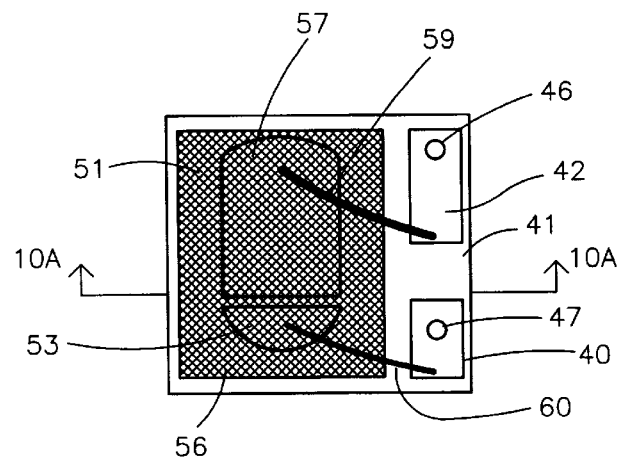
FIG. 9 is a top view of the structure shown in FIG. 8 after wire bonding of the die is performed.

Following the formation of the various bond pads on surfaces of ceramic substrate 32, component bonding (block 13) including processes such as die bonding (block 14) and/or wire bonding (block 16) are performed as shown in FIGS. 8–10. The die 56 (which may be a FET die as shown in FIG. 15) has a first side 51 and a second side 55. The second or back side 55 of die 56 is an active area contact region. Additional active area contact regions 53, 57 are found on first or front side 51 of die 56. FIG. 7 shows the application of a conductive material 54 on die bond pad 39 for use in the die bonding of die 56 to die bond pad 39 as shown in the top view structure of FIG. 8.

Figure 10A:
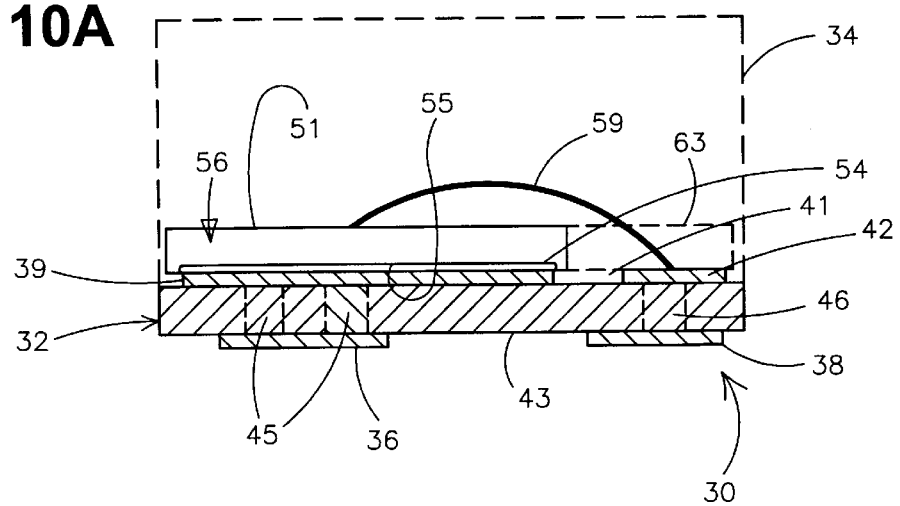
FIG. 10A is a cross-section view along line 10—10A of FIG. 9 including an encapsulant formed to encapsulate various elements of the structure of FIG. 9.

FIG. 9 and the cross-section view of FIG. 10A taken at line 10A—10A of FIG. 9 show the die 56 fixedly positioned on die bond pad 39 using the conductive material 54. The conductive material 54 may be any conductive material such as a conductive adhesive material, e.g., silver filled epoxy or any other conductive epoxy, or a solder paste. As such, active area contact region on the back side 55 of the die 56 is electrically connected via the conductive epoxy 54, the die bond pad 39, and vias 45 to the package connection pad 36 on the second side 43 of ceramic substrate 32.

Further, FIGS. 9 and 10A illustrate wire bonding of the two active area contact regions 53, 57 of die 56 to wire bond pads 40, 42, respectively. In FIG. 9, region 57 is electrically connected via wire 59 to wire bond pad 42 and thus electrically connected to package connection pad 38 by way of via 46. Likewise, region 53 of die 56 is electrically connected to wire bond pad 40 by wire 60 and further connected to package connection pad 37 by way of via 47. The wire bonding may be performed using a variety of wires, including one or more wires per connection of active regions of the die to wire bond pads.

For example, as illustrated in FIG. 10A, the region of the second side 55 of the die 56 is connected to package connection pad 36 by vias 45, and the regions 57, 53 on first side 51 of the die 56 are connected to package connection pads 38, 37 by vias 46, 47, respectively. However, the present invention may also be used for a die that only has electrical contact regions on a single side, or contact regions that are located at various positions on the die. One skilled in the art will recognize that the location of die and/or wire bond pads will vary and that the type of electrical connection to the vias will vary, depending upon the location of the contact regions of the die. For example, if only contact regions exist on the front side of the die, then only wire bonding may be necessary with a nonconductive adhesive being used to hold the die in place.

Figure 10B:
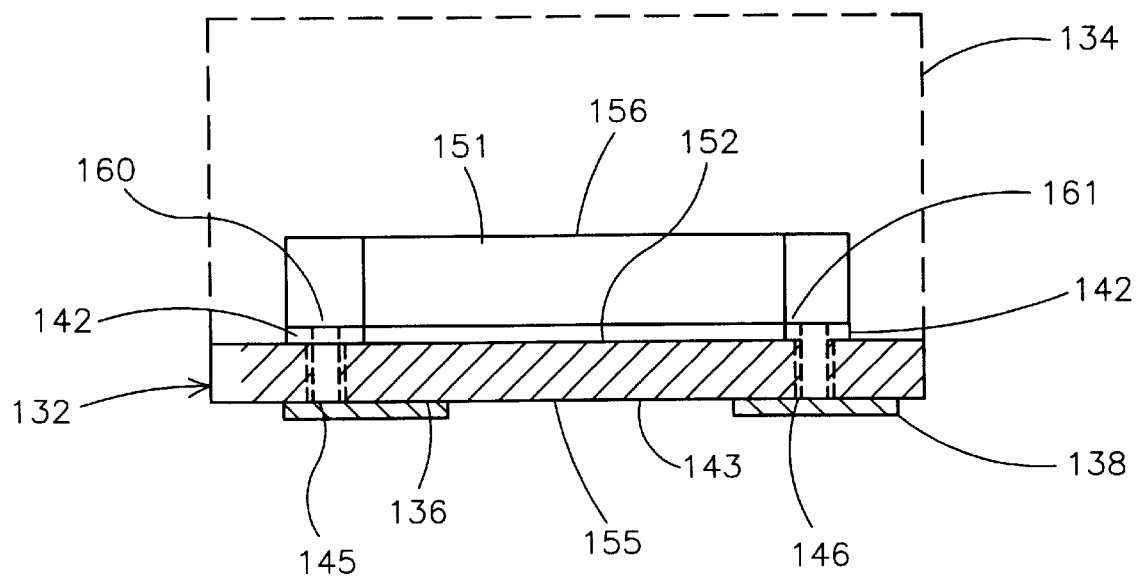
FIG. 10B is a cross-section view showing an alternative embodiment including a printed wiring board and a high voltage surface mount component.

FIG. 10B illustrates the use of a PWB substrate 132 to package a surface mount component 156. The surface mount component 133 may be any component as described previously herein such as the high voltage surface mount capacitor as shown in FIG. 16. The PWB substrate 132 may be any suitable PWB provided with a plated through hole via pattern. The illustrative substrate 132 includes via 145 and via 146. The thickness of the substrate 132 will vary. Preferably, the thickness of the substrate is about 0.010 inches (0.254 millimeters) +/−20 percent. The plated through hole vias will have a diameter that varies depending on the current carrying 1o capability required by the high voltage component 156 mounted thereon. For example, the via hole diameters may be about 0.010 inches (0.254 millimeters) +/−20 percent.

The substrate 132 shown in FIG. 10B may be one of an array of substrate device formation regions as will be apparent from the description below. With use of such an array, mass production of encapsulated packages is allowed.

The conductive pads 139, 142 are provided in contact with the plated through hole vias 145, 146, respectively, on a first side 141 of the substrate 132 by conventional processing, e.g., with use of a solder mask. Solderable package connection pads 136, 138 are provided on the second side 143 of the substrate 132 in contact with the vias 145, 146, respectively. Any materials that can withstand soldering processes are suitable for use as the package connection pads 136, 138.

Following the provision of the substrate 132 (block 12), component bonding (block 13) is performed to electrically connect the surface mount component 156 to the conductive package connection pads 136, 138. The surface mount component 156 having two or more electrical connection regions at positions on the component, may be electrically connected to the bond pads 139, 142 using any suitable technique, e.g., wire bonding, die bonding, soldering, etc. In many cases, the surface mount component 132 will have contact regions, like contact regions 160, 161 as shown in FIG. 10B. Such contact regions are then preferably electrically connected using solder paste and reflow with the component held to the board using an adhesive 152. Such solder paste and reflow processes are commonly used to mount surface mount packages on printed circuit boards. The packaging of surface mount components may be referred to as a repackaging of the already packaged components.

One skilled in the art will recognize that the electrical connection of die or surface mount components to conductive bond pads on the first side of the substrate, e.g., ceramic, PWB, can be performed using any number of attachment techniques. The present invention contemplates the use of wire bonding alone, wire bonding and die bonding in combination, or die bonding alone, in addition to other electrical connection mounting methods, e.g., solder paste and reflow, tape bonding, etc.

FIG. 10A and FIG. 10B further show, in dashed line, encapsulant material 34, 134 for encapsulating the elements located on the first side 41, 14 of substrate 32, 132, respectively. Generally, the encapsulation step (block 18) of the chip scale packaging method 10 shown in FIG. 1 includes two steps and is best described with reference to FIGS. 11–13 wherein an array of encapsulated packages 30 are produced. However, one skilled in the art will recognize that substantially the same encapsulation steps may be used to perform encapsulation of a single device.

Figure 2:
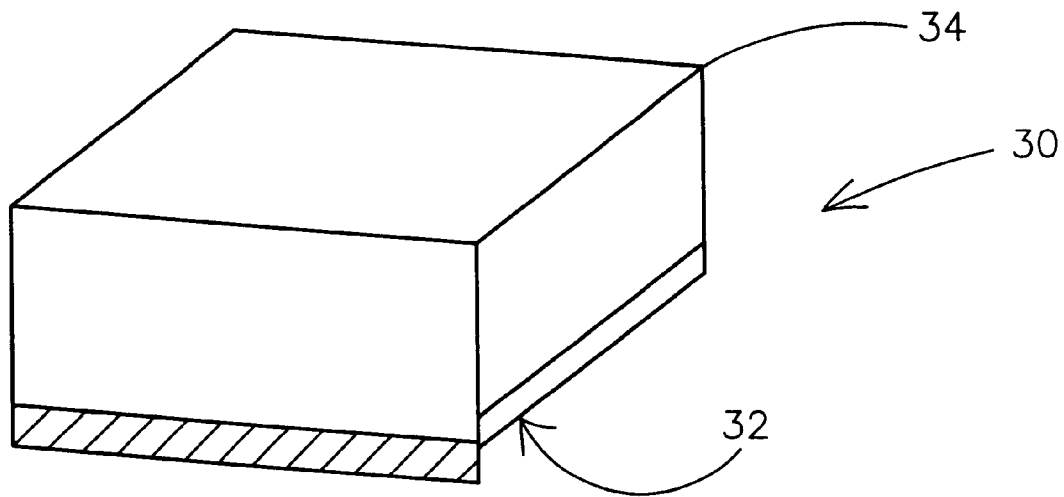
FIG. 2 is a perspective view of one illustrative embodiment of an encapsulated package resulting from the method of FIG. 1.
Figure 11:
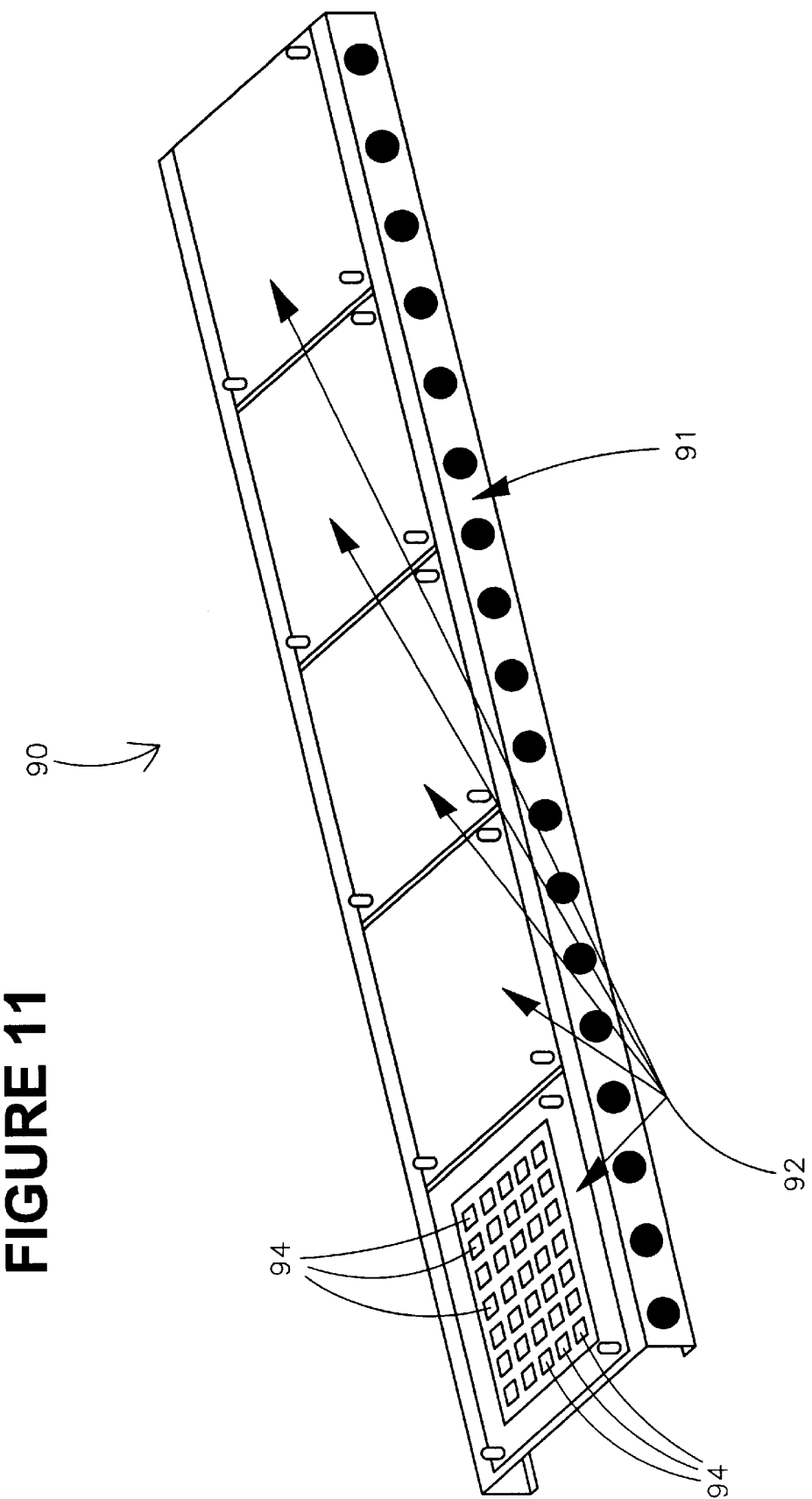
FIG. 11 shows a carrier for use in the method of FIG. 1, including substrates having an array of substrate device formation regions for mass producing encapsulated packages.

FIG. 11 shows a carrier 90 for use in mass production of multiple arrays of encapsulated packages 30 (FIG. 2). The carrier 90 includes a standard carrier device 91 used for in-line processing. The carrier 90 includes multiple ceramic substrates 92 which are many times the size of a single encapsulated package 30. For example, the ceramic substrate 92 may be about 2.4 inches by 2.4 inches (6.1 centimeters by 6.1 centimeters). Each ceramic substrate 92 held in the assembly 90 includes an array of ceramic substrate device formation regions 94 in which one or more high voltage components are attached as described above with reference to FIGS. 4–10. One skilled in the art will recognize that although the description to follow regarding mass production of devices is provided with respect to a ceramic substrate, that the description is equally applicable to other types of substrates as well.

Figure 12:
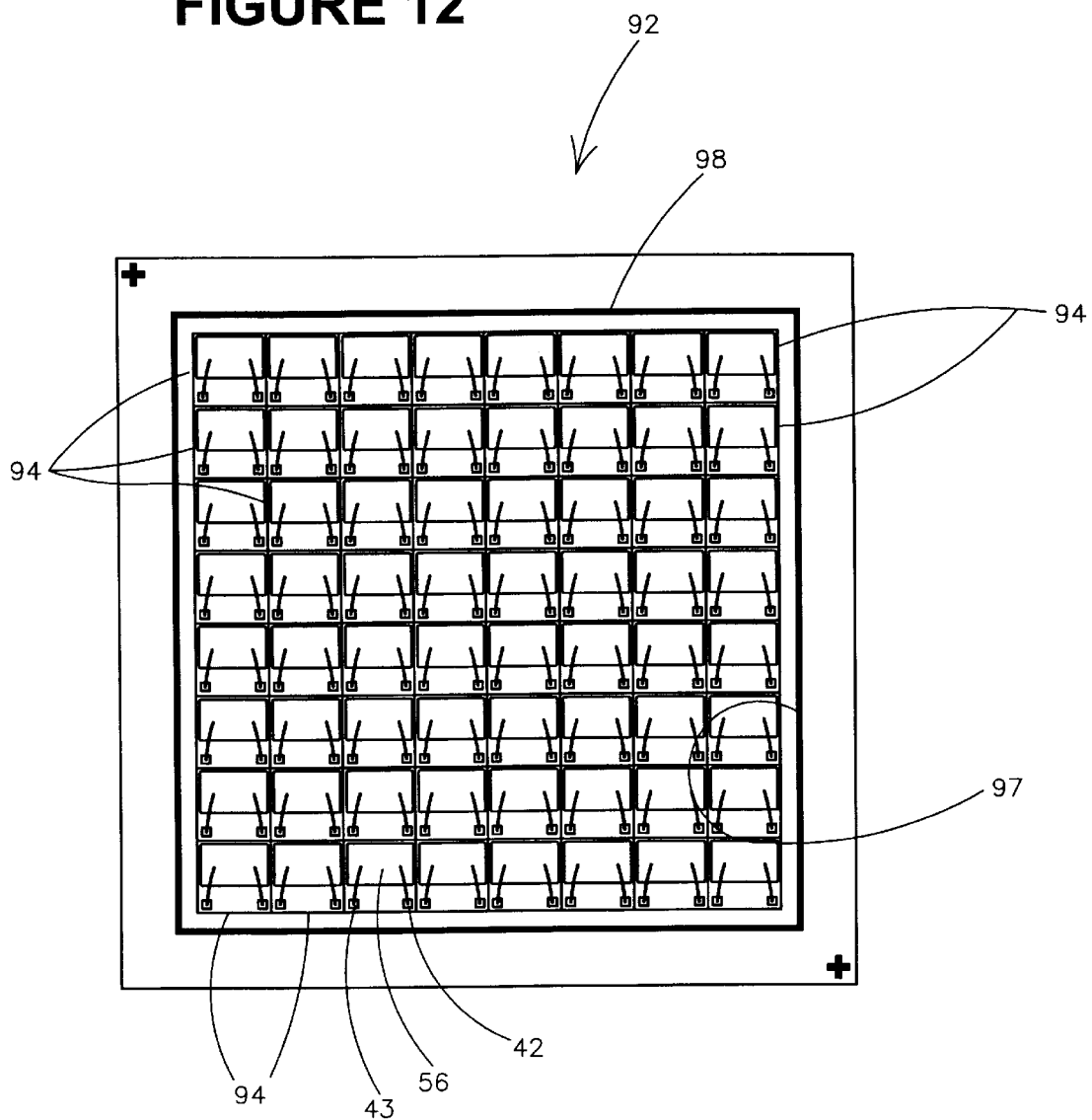
FIG. 12 is a top view of one particular substrate of the carrier shown in FIG. 11 having a high voltage component electrically connected in each region of the array of device formation regions using the method of FIG. 1.

FIG. 12 shows sixty-four (64) device formation regions 94 of a single ceramic substrate 92 for production of sixty-four (64) encapsulated packages 30. Further, FIG. 12 illustrates each device formation region 94 including a die 56 wire bonded to wire bond pads 42, 43 and die bonded to a die bond pad (not shown), as previously described with reference to FIGS. 9 and 10. With the array of ceramic substrate device formation regions 94 having a high voltage component attached therein and electrically connected to package connection pads on the second side 43 of ceramic substrate 32, the encapsulation step (block 18) for production of an array of encapsulated packages 30 is performed in two steps.

Figure 13:
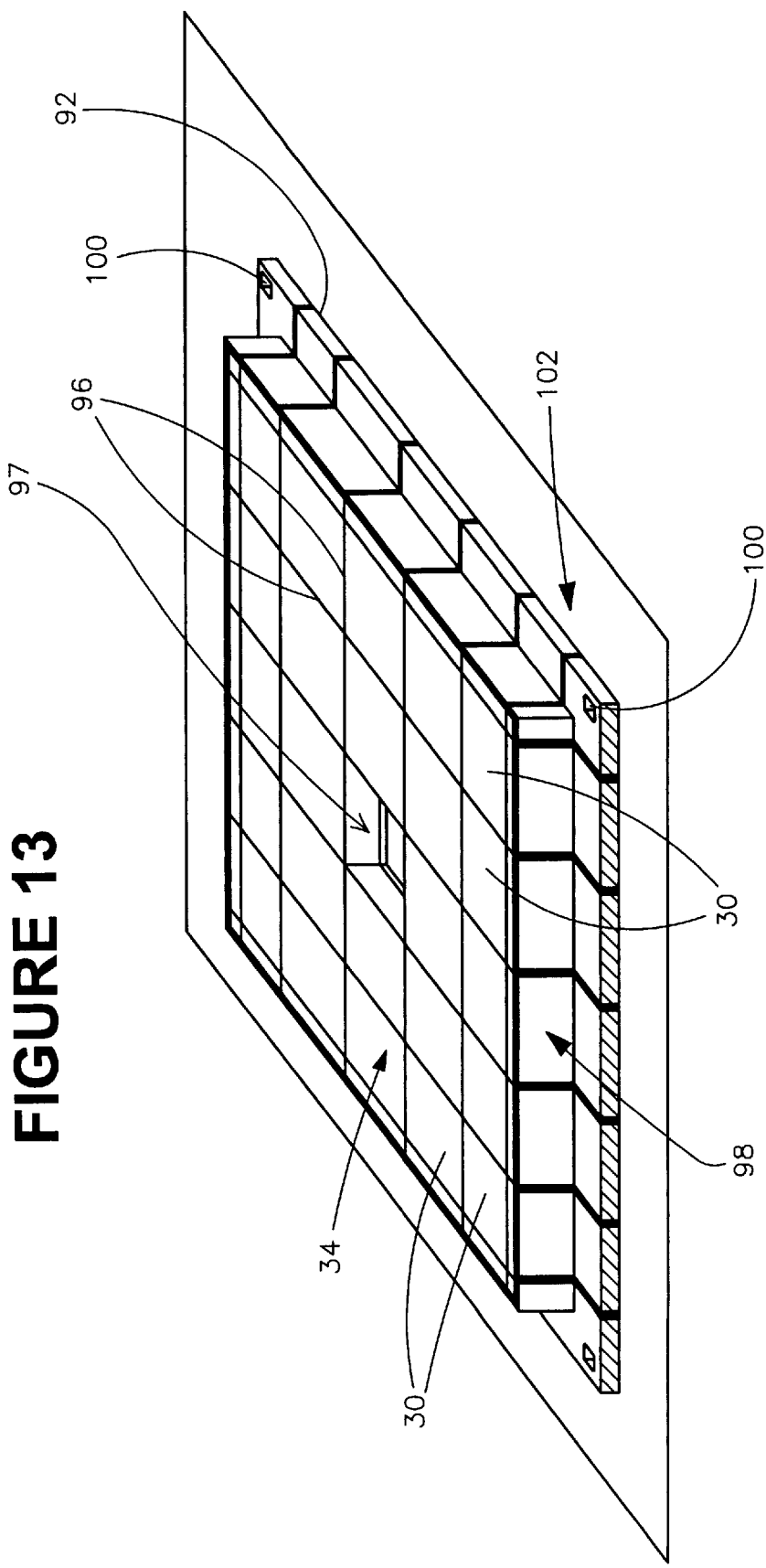
FIG. 13 is a perspective view of the particular substrate of the substrate carrier shown in FIG. 12 encapsulated and singulated according to the present invention.

As shown in FIG. 13, first, a dam structure 98 is provided, e.g., formed or positioned, around the perimeter of the device formation regions 94 defining an interior space 97 over the device formation regions 94. For example, an epoxy dam may be dispensed around the perimeter of the array of device formation regions 94. Alternatively, a rigid frame, e.g., plastic frame or metal frame, may be used as the dam structure 98.

The second step of the encapsulation process (block 18) involves backfilling the interior space 97 defined by the dam 98 with insulating material, i.e., encapsulating material 34, to encapsulate the array of device formation regions 94; each region having a high voltage component bonded therein. The encapsulating material 34 acts as an insulator for high voltage applications and serves as the body packaging for the encapsulated package 30, after the material is cured (if necessary).

The encapsulating material 34 used to fill the interior space 97 is preferably of a low viscosity. Preferably, the viscosity is less than about 120,000 centipoise (determined at 25 degrees centigrade using a Brookfield RVF spindle #7 at a speed of 20 cycles per second). With such lower viscosity materials, air bubbles will be minimized as the die coat dam 98 is backfilled with the encapsulant material 34. By eliminating the air bubbles therein, voids in the cured material are minimized. Thus, the chance of arcing occurring as a result of high voltages is minimized.

Further, encapsulating material 34 is of a high dielectric strength, preferably greater than about 100 volts per mil. More preferably, the dielectric strength of the encapsulanting material 34 is greater than about 400 volts per mil, particularly for components operable at potentials greater than 100 volts. Having an encapsulant of such dielectric strength is required to suppress surface arcing and increase the reliability of the package 30. For example, the encapsulating material 34 may be a material available under the trade designation Dexter 4402 from Dexter Corporation (Industry, Calif.).

The encapsulating material 34 is also a low stress material or, in other words, has a coefficient of thermal expansion that matches the coefficient of thermal expansion of the substrate being used, e.g. ceramic, PWB, etc. This relieves the stresses between the encapsulant and the substrate.

Once the encapsulating material 34 is cured in accordance with a curing process which will depend upon the material being used, the array of device formation regions 94 are singulated (block 20, FIG. 1) resulting in encapsulated packages 30. One such package is shown removed from the array of FIG. 13. The process of singulating or dicing the array to attain encapsulated packages 30 may be performed using any known singulation technique along singulation lines 96. For example, the singulation may be performed by wafer sawing. In such a wafer sawing process, the ceramic substrate 92 including the encapsulated array is mounted onto a wafer saw frame using tape 102 and aligned using alignment holes 100. The sawing is then performed using the wafer saw resulting in the individual encapsulated packages 30. Further, other methods of singulation may include laser scribing and breaking, laser cutting, or any other technique for singulating the encapsulated array resulting in encapsulated packages 30.

After singulation (block 20), the encapsulated packages 30 are removed from the tape 102 and placed into a packaging apparatus, e.g., a tube, for optional testing (block 22). The packaged device can then be fully tested for all AC and DC parameters. Contact is made to the solderable connection pads 36–38 by any particular means: pullable pins, particle interconnect pads, or probe needles. The solderable package connection pads 36–38 are designed to handle maximum current and stand-off voltage in open air.

Figure 3:
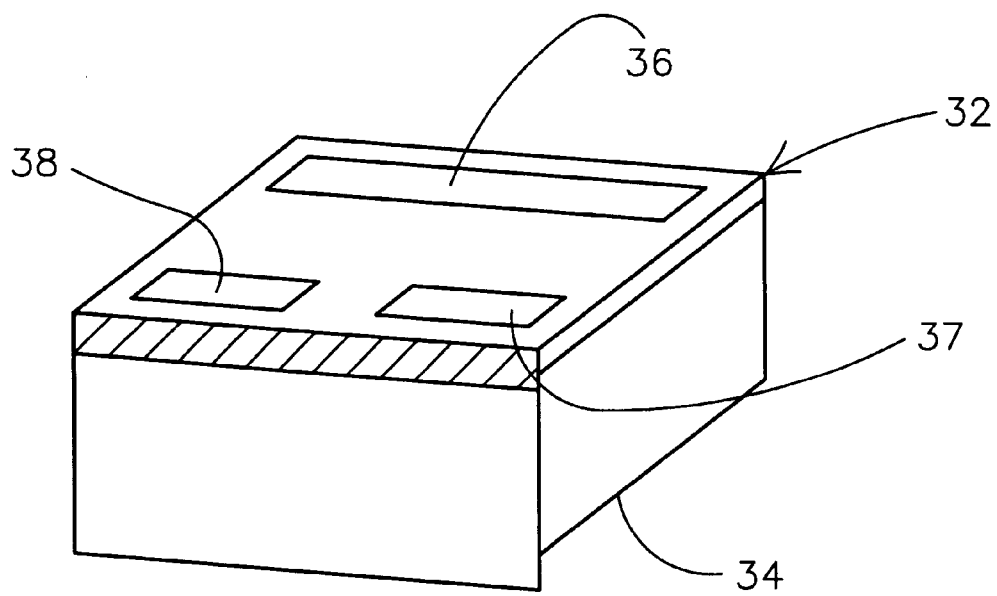
FIG. 3 is a bottom perspective view of the encapsulated package of FIG. 2.

The surface mountable encapsulated package 30, as shown in FIG. 2 and FIG. 3, may then be used or connected to a printed circuit board or any other interconnection surface using standard surface mount technology processes. For example, solder paste may be printed on a set of matching pads on the printed circuit board, with the component being placed on the solder paste. Thereafter, the solder is reflowed and the assembly cleaned.

The present invention allows high voltage, high current components to be packaged as a surface mount chip scale packages with a very small footprint. In accordance with the method described above, a chip scale package may have a package to component ratio size in the range of about 1.2 to about 3.0, generally depending upon the size of the component being packaged. Such a package to size ratio is determined from the x-y surface area of the high voltage component and the package. The component or die would have to be at least 280 mils square to meet the 1.2 ratio. A conventional package for a high voltage component or die typically is 4 to 5 times larger than the component or die, e.g., leadless chip carrier packages. Such lower package to component size ratios are accomplished using the process described above which allows for minimization between elements of the package, e.g., the use of high dielectric strength encapsulant allows for minimized spacing between wire bond pads.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to high voltage components being wire bonded to bond pads formed on the substrate. In addition, surface mount packages may be repackaged as described with reference to FIG. 10B. As such, the present invention further includes within its scope other methods of making and using the invention described herein above.

What is claimed is:

1. A method of packaging one or more high voltage components, the method comprising the steps of:

providing a substrate having a first substrate side and a second substrate side and including one or more device formation regions, each device formation region of the substrate formed by:

extending at least two conductive vias through said substrate from said first substrate side to said second substrate side;

forming a conductive bond pad formed on the first substrate side in electrical contact with each conductive via; and forming a conductive package connection pad on the second substrate side in electrical contact with each conductive via;

providing at least one high voltage component adapted to fit to each such device formation region having at least two electrical terminals and operable with a potential greater than about 50 volts applied across said two electrical terminals;

electrically connecting said at least two electrical terminals of said high voltage component to two conductive bond pads in each of the device formation regions on the first substrate side, the high voltage component being operable with a potential greater than about 50 volts applied through conductive package connection pads and said two electrical terminals;

forming an encapsulating material over the one or more device formations regions of the substrate including the at least one high voltage component and the conductive bond pads in each device formation region, the encapsulating material after curing, having a dielectric constant greater than about 100 volts per mil; and singulating the encapsulated device formation regions resulting in one or more encapsulated packages enclosing at least one high voltage component within said encapsulating material, wherein the encapsulated package has a package to component size ratio in the range of about 1.2 to about 3.0.

2. The method of claim 1, wherein the one or more device formation regions include an array of device formation regions.

3. The method of claim 2, wherein the step of forming an encapsulating material over the one or more device formations regions of the substrate includes:

providing an encapsulation dam about a perimeter of the array of device formation regions on said first substrate side;

filling an interior space defined by the dam with a liquid encapsulating material; and curing the encapsulating material to solidify it over said first substrate side and said one or more high voltage components.

4. The method of claim 1, wherein:

the step of forming a conductive bond pad on the first substrate side further comprises the steps of:
  forming at least one or more conductive die bond pad in electrical contact with at least a first via; and
  forming at least one conductive wire bond pad formed in electrical contact with at least a second via; and the step of electrically connecting the at least one high voltage component in each device formation region further comprises the steps of:
  attaching at least a first active contact region of the at least one high voltage component to the conductive die bond pad using a conductive attachment material; and
  electrically connecting at least a second active contact region of the at least one high voltage component to the conductive wire bond pad.

5. The method of claim 1, wherein the at least one high voltage component includes a surface mount component having one or more contact regions each enabling electrical connection to one of the conductive bond pads formed on the first substrate side.

6. The method of claim 1, wherein the encapsulating material has a viscosity less than about 20,000 poise at 60 degrees centigrade on a Brookfield spindle No. 7 at a speed of 20 centimeters per second.

7. The method of claim 1, wherein the high voltage component is operable with a potential greater than about 100 volts applied across any two electrical terminals of the component, and the encapsulating material after curing has a dielectric strength greater than about 400 volts per mil.

8. The method of claim 1, wherein the substrate is a ceramic substrate and the one or more conductive vias defined therethrough are completely filled with conductive material.

9. The method of claim 1, wherein the substrate is a printed wiring board with the one or more conductive vias defined therethrough being plated though hole vias.

10. The method of claim 4, wherein the high voltage component is operable with a potential greater than about 100 volts applied across any two electrical terminals of the component, and the encapsulating material has a dielectric strength greater than about 400 volts per mil.

11. The method of claim 4, wherein the high voltage component is operable with a potential between about 100 volts and about 1000 volts applied across any two electrical terminals of the component; and the encapsulating material has a dielectric strength greater than about 400 volts per mil.

12. The method of claim 1, wherein the high voltage component is operable with a potential between about 100 volts and about 1000 volts applied across any two electrical terminals of the component; and the encapsulating material has a dielectric strength greater than about 400 volts per mil.

13. A method of forming an implantable medical device comprising the steps of:

providing a housing of the implantable medical device;

enclosing a source of electrical power within the housing;

providing a substrate having a first substrate side and a second substrate side and including one or more device formation regions, each device formation region of the substrate formed by:
  extending at least two conductive vias through said substrate from said first substrate side to said second substrate side;
  forming a conductive bond pad formed on the first substrate side in electrical contact with each conductive via; and
  forming a conductive package connection pad on the second substrate side in electrical contact with each conductive via;

providing at least one high voltage component adapted to fit to each such device formation region having at least two electrical terminals and operable with a potential greater than about 50 volts applied across said two electrical terminals;

electrically connecting said at least two electrical terminals of said high voltage component to two conductive bond pads in each of the device formation regions on the first substrate side, the high voltage component operable with a potential greater than about 50 volts applied through conductive package connection pads and said two electrical terminals;

forming an encapsulating material over the one or more device formations regions of the substrate including the at least one high voltage component and the conductive bond pads in each device formation region, the encapsulating material after curing having a dielectric strength greater than about 100 volts per mil;

singulating the encapsulated device formation regions resulting in one or more encapsulated packages enclosing at least one high voltage component within encapsulating material, whereby the encapsulated package has a package to component size ratio in the range of about 1.2 to about 3.0; and enclosing at least one encapsulated package within the housing coupled at the conductive package connection pads with said source of electrical power to supply said potential greater than about 50 volts thereto.

14. The method of claim 13, wherein the high voltage component is operable with a potential greater than about 100 volts applied across any two electrical terminals of the component, and the encapsulant material has a dielectric strength greater than about 400 volts per mil.

15. The method of claim 13, wherein the high voltage component is operable with a potential between about 100 volts and about 1000 volts applied across any two electrical terminals of the component; and the encapsulant material has a dielectric strength greater than about 400 volts per mil.

* * * * *